United States Patent [19]

Parr et al.

[11] Patent Number: 4,797,441
[45] Date of Patent: Jan. 10, 1989

[54] DICHLORO (ACETIC OR PROPIONIC) ACID ARYL ESTER FLAME RETARDANTS

[75] Inventors: William J. Parr, Naperville, Ill.; Peter Hope, Twello, Netherlands

[73] Assignee: Akzo N.V., Netherlands

[21] Appl. No.: 61,932

[22] Filed: Jun. 11, 1987

[51] Int. Cl.$^4$ .............. C07C 69/63; C07C 147/115; C07C 149/40; C08K 5/10
[52] U.S. Cl. .................... 524/288; 524/289; 524/411; 560/138; 560/140; 560/141; 560/228
[58] Field of Search ............... 524/289, 288; 560/138, 560/140, 141, 229, 228

[56] References Cited

U.S. PATENT DOCUMENTS

| | | | |
|---|---|---|---|
| 3,006,967 | 10/1961 | Newcomer et al. | 560/228 |
| 3,231,603 | 1/1966 | Hennis et al. | 524/326 |
| 3,883,481 | 5/1975 | Kopetz et al. | 524/288 |
| 4,170,711 | 10/1979 | Orlando et al. | 524/288 |
| 4,178,410 | 12/1979 | Tomita | 524/171 |
| 4,258,153 | 3/1981 | Yomamoto et al. | 524/539 |

FOREIGN PATENT DOCUMENTS 1543541 11/1969 Fed. Rep. of Germany .
1281937 7/1972 United Kingdom .

Primary Examiner—Veronica P. Hoke
Attorney, Agent, or Firm—Jeffrey S. Boone

[57] ABSTRACT

The present disclosure relates to novel compounds of the formula:

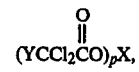

where Y is a hydrogen atom or a metal group and p=1 or 2, and when p=1,

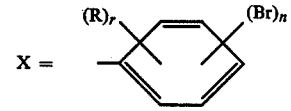

n=2, 3, 4 or 5 and n+r≦5 and when p=2,

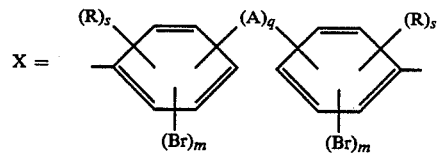

m=2, 3 or 4 and m+s≦4 and q=0 or 1, where R represents a lower alkyl group containing 1 to 3 carbon atoms, and when q=1, A has the meaning of a substituted or unsubstituted alkylidene group containing 1 to 3 carbon atoms, SO$_2$, S or O; fire retardant polymer compositions in which these compounds are incorporated, and shaped articles that are entirely or partly made up of such fire retardant polymer compositions.

9 Claims, No Drawings

DICHLORO (ACETIC OR PROPIONIC) ACID ARYL ESTER FLAME RETARDANTS

The invention relates to novel chlorinated carboxylic acid esters of brominated aromatic phenols, to fire retardant polymer compositions in which these compounds are incorporated, and to shaped articles that are entirely or partly made up of such fine retardant polymer compositions.

The use of chlorinated carboxylic acid esters of brominated phenols as fire retardants is well known in the art and disclosed, among other places, in European Pat. No. 73 539. Though the trichlorobutyrate esters mentioned therein are found to be suitable fire retardants in polymers such as polystyrene and ABS, a continuous need is felt for the reduction of the quantities thereof to be incorporated in the polymers.

Another relevant document is German Patent Specification No. 15 43 541 in which in Example 6 some allusion is made to the flame retardant properties of the trichloroacetate ester of tetrabromobisphenol A. However, contrary to the trichlorobutyrate ester of tetrabromobisphenol A disclosed in EP No. 73 539, this compound has been found to be unsuitable because of its corrosion promoting properties.

Thus, it would be desirable to have a fire retardant compound which can be used in lower amounts than, and is less corrosive than the prior art compounds.

The invention provides novel compounds of the formula:

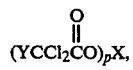

where Y has the meaning of a methylgroup or hydrogen atom and p=1 or 2, and when p=1,

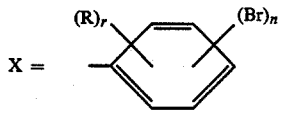

wherein n=2, 3, 4 or 5 and n+r≦5 and when p=2,

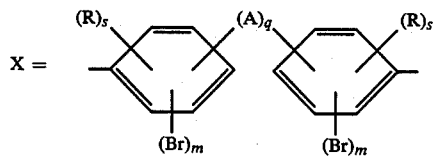

wherein separatly for each aromatic ring m=2, 3 or 4 and m+s≦4
and q=0 or 1, where R represents a lower alkyl group containing 1 to 3 carbon atoms, and when q=1, A has the meaning of a substituted or unsubstituted alkylidene group containing 1 to 3 carbon atoms, SO$_2$, S or O.

The novel compounds according to the invention have been found to be particularly suitable for use as fire retardant agents in polymer compositions based on polystyrene and copolymers thereof. Examples of materials which can be particularly effective rendered fire retardant with the novel compounds of the invention include polyolefins, polyurethanes, unsaturated polyester resins and polyacrylate resins.

In particular, exceptional fire retardant characteristics are imparted by the products of the invention to high impact polystyrene and acrylonitrile butadiene styrene copolymer (ABS), of which polymers it is known that they cannot readily be rendered fire retardant.

Moreover, it has been found that when the fire retardant polymer compositions are processed at elevated temperatures (200° to 250° C.), the compounds according to the invention hardly, if at all, give rise to discoloration upon decomposition of the bromine compounds or to corrosion upon contact with metal surfaces.

In view of the detrimental nature of the trichloroacetate esters of the aformentioned German patent, it is considered quite surprising that the dichloroacetate ester of tetrabromobisphenol A is far less prone to polymer discoloration or corrosion and that the amount thereof to be incorporated in ABS is less than that of the known trichlorobutyrate ester of tetrabromobisphenol A taught in the aformentioned European patent.

With respect to the preparation, the favorable compatibility and the fire retardant properties it is preferred that use should be made of compounds where in the aromatic ring X has one of the following structures:

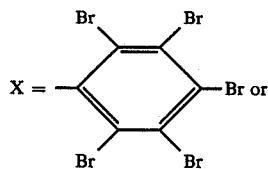

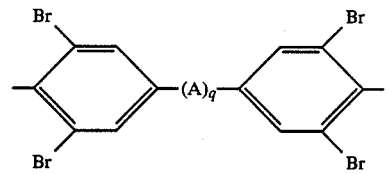

Generally favorable results are obtained when A has the meaning of an isopropylidene group.

In general, satisfactory fire retardant polymer compositions are obtained by incorporation therein of 1 to 25% by weight of the novel chlorine and bromine-containing compounds according to the invention, and 0.5 to 15% by weight of a synergistically active antimony, arsenic, zinc and/or tin compound, said amounts being calculated on the weight of the resulting fire retardant polymer composition. Examples of suitable antimony, arsenic, zinc and/or tin compounds include antimony oxide, antimony chloride, antimony bromide, antimony iodide, antimony oxychloride, arsenic trioxide, arsenic pentoxide, zinc sulphate, zinc oxide, zinc borate and tin (II) oxide. Optimum results are obtained when into these fire retardant polymer compositions the antimony compound Sb$_2$ is incorporated in an amount of 25 to 75, and preferably 33 to 6% by weight, based on the novel compounds of the present invention.

Preparation of the novel compounds according to the invention may be carried out in a manner known from the chemical technology for analogous compounds.

In a preferred procedure dichloroacetyl chloride or 2,2-dichloropropionyl chloride is caused to react with a bromated phenol. For best results the reaction is carried out in an inert solution in the presence of a base such as triethylamine or pyridine. Although the temperature of the reaction is not critical, it is preferred that the reaction should be carried out within the range of −10° to 120° C. As the reaction is exothermic, it is preferred to add the acid chloride gradually to the reaction mixture, with cooling, if desired. Heating to higher temperature can be advantageous in certain intances.

The invention will be further described in, but not limited to the following examples.

EXAMPLE I

Preparation of bis-dichloroacetyl ester of tetrabromobisphenol A 108,8 parts of tetrabromobisphenol A, 32 parts of pyridine, 0.5 parts of 4-dimethylaminopyridine and 500 parts of dichloromethane were cooled to 5° C., with stirring, and the system was flushed with nitrogen. Subsequently, a solution of 60 parts of dichloroacetyl chloride in 50 parts of dichloromethane was added dropwise whilst maintaining the temperature below 15° C. When the addition was complete, the mixture was allowed to cool to room temperature (20° C.), after which it was stirred for another 3 hours. After addition of 300 parts of water the organic layer was separated, dried over magnesium sulphate and evaporated to give 144 parts of the title compound (compound A), which was a cream solid of melting point 170°–172° C. Recrystallization from chloroform/ethanol afforded the bis-dichloroacetyl ester of tetrabromobisphenol A as a white solid having a melting point of 172°–173° C. (compound A).

The same procedure was used in preparing the bis-(2,2-dichloropropionyl) ester of tetrabromobisphenol A (compound B) having a melting point of 223°–225° C. and the dichloroacetyl esters of 2,4,6-tribromophenol having a melting point of 75°–77° C. and of pentabromophenol having a melting point of 144°–146° C.

EXAMPLE II

In this example the fire retardant effect of the compounds according to the invention is compared with that of the bis-trichlorobutyrate ester of tetrabromobisphenol A (compound C) known from European Pat. No. 73 539.

Two parts of the compounds A, B and C were mixed with one part of antimony oxide and, in the amounts indicated below, added to ABS polymer. The amount of fire retardant material was varied in each experiment until the resulting material satisfied a Vo class I rating, use being made of the UL 94 test. Mixing with the ABS polymer was carried out on a 2 roll mill for 10 minutes at 160°–170° C. and thereafter the polymer mix was pressed into a 2 mm thick plaque at 200° C.

The results of the experiments are given in the table below.

TABLE I

| Compound | wt. % fire retardant for Vo | wt. % $Sb_2O_3$ | m moles halogen per 100 g compos. | wt. % halogen |
|---|---|---|---|---|
| A | 12.5 | 6.2 | 131 | 7.54 |
| B | 13.0 | 6.5 | 131 | 7.56 |
| *C | 13.5 | 6.7 | 151 | 8.07 |

*Not an example of the invention.

From the above table it is clear that when use is made of the compounds A and B according to the invention the halogen content of the polymer compositions that are to be rendered fire retardant can be reduced to a remarkable extent. It will be obvious that for reasons of both economy and environmental protection the use of polymer compositions containing a smallest possible amount of halogen has been found to become increasingly important.

EXAMPLE III

Samples of the plaques obtained as described in Example II were repressed in a heated compression moulding press, sandwiched between sheets of degreased mild steel at a temperature in the range of 230° to 250° C. After 5 minutes the test specimens were separated from the mild steel and the mild steel inspected for corrosion on a 1 to 5 scale. The rating 1 indicates that the steel is bright and uncorroded; the rating 2 is indicative of a dull steel plate; the rating 3 points to slight corrosion of the steel; the rating 4 means moderate corrosion of the steel plate; the rating 5 means heavy corrosion of the steel. The products A and B according to the invention were compared with compound C known from European Pat. No. 73 539 and compound D, viz. the bis-trichloroacetate ester of tetrabromobisphenol A, described in Example 6 of German Patent Specification No. 15 43 541.

TABLE II

| Compound | wt. % fire retardant | wt.% $Sb_2O_3$ | Corrosion 230° C. | Corrosion 250° C. |
|---|---|---|---|---|
| A | 12.5 | 6.2 | 3 | 3 |
| B | 13.7 | 6.8 | 3 | 3 |
| *C | 13.5 | 6.7 | 3–4 | 3–4 |
| *D | 11.0 | 5.5 | 4–5 | 5 |

*Not an example of the invention.

The results mentioned in the above table clearly show that as compared with compound C containing three chlorine atoms in the position gamma to the carbonyl carbon atom, compound D containing three chlorine atoms in a position alpha to the carbonyl carbon atom causes greatly increased corrosion of the mild steel. Therefore, it must be considered particularly surprising, that as compared with compound C, compounds A and B containing two chlorine atoms in the position alpha to the carbonyl carbon atom cause reduced corrosion.

EXAMPLE IV

In this example it is demonstrated that the compounds according to the invention are very stable to UV-radiation.

In various experiments UV-stability was assessed by conducting a "Xenotest 150", use being made of accelerated weathering test equipment. The discolouration was assessed after periods of 215 and 407 hours on a 1 to 6 scale, where 1 is a white, 2 a pale beige, 3 a beige, 4 a dark beige or yellow, 5 an orange and 6 an orange/brown polymer. The results obtained are presented in the table below.

TABLE III

| Compound | wt. % | % $Sb_2O_3$ | Original colour | Colour after irradiation for 215 hours | Colour after irradiation for 407 hours |
|---|---|---|---|---|---|
| A | 12.5 | 6.2 | 1 | 2 | 3 |
| *C | 13.5 | 6.7 | 1 | 3 | 4 |

*Not an example of the invention

The above results clearly show that of compound A according to the invention the UV-stability is better than that of the known trichlorobutyrate ester of tetrabromobisphenol A (compound C).

We claim:

1. A compound of the formula

where Y has the meaning of a methyl group or hydrogen atom and p=1 or 2, and when p=1,

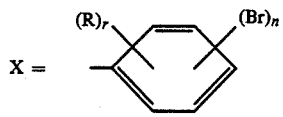

wherein n=2,3,4 or 5 and n +r+5 and when p=2,

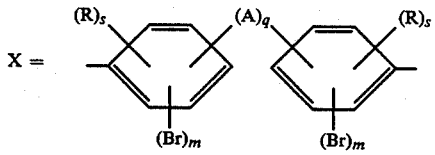

wherein separately for each aromatic ring m=2,3 or 4 and m+s≦4 and q=O or 1, where R is a lower alkyl group containing 1 to 3 carbon atoms, and when q=1, A is a substituted or unsubstituted alkylidene group containing 1 to 3 carbon atoms, $SO_2$, S or O.

2. The compound of claim 1 wherein A is an isopropylidene

3. The compound claim 1 wherein

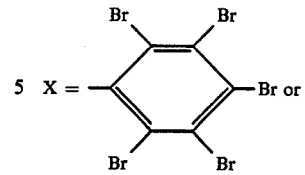

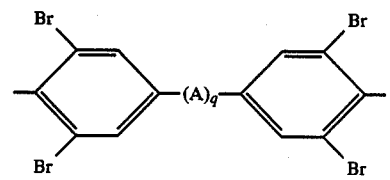

4. A fire retardant polymer composition (a) an organic polymer comprising a polyolefin, polyurethane, unsaturated polyester resin, polystyrene, or copolymers thereof, and (b) a fire retardant amount of the compound of claim 1.

5. A fire retardant polymer composition comprising (a) an organic polymer comprising a polyolefin, polyurethane, unsaturated polyester resin, polystyrene, or copolymers thereof, and (b) a fire retardant amount of the compound of claim 2.

6. A fire retardant polymer composition comprising (a) an organic polymer comprising a polyolefin, polyurethane, unsaturated polyester resin, polystyrene, or copolymers thereof, and (b) a fire retardant amount of the compound of claim 3.

7. The fire retardant polymer composition of claim 4, wherein the composition contains 1–25% by weight of the compound and 0.5–15% by weight of antimony oxide, said amounts being based on the weight of the resulting fire retardant composition.

8. The fire retardant polymer composition according of claim 7 wherein the antimony oxide is used in an amount of 25 to 75% by weight, based on the weight of the compound.

9. A shaped article comprising an object formed from the fire retardant composition of claim 4.

* * * * *